(12) United States Patent
Hildwein et al.

(10) Patent No.: US 8,025,633 B2
(45) Date of Patent: Sep. 27, 2011

(54) ARRANGEMENT FOR EXTRACORPOREAL CIRCULATION OF BLOOD

(75) Inventors: Helmut Hildwein, Vöhringen (DE); Jens Schiele, Fridingen (DE); Jutta Kiener, Hechingen (DE)

(73) Assignee: Gambro Lundia AB, Lund (SE)

( * ) Notice: Subject to any disclaimer, the term of this patent is extended or adjusted under 35 U.S.C. 154(b) by 602 days.

(21) Appl. No.: 12/066,477

(22) PCT Filed: Sep. 1, 2006

(86) PCT No.: PCT/SE2006/001011
§ 371 (c)(1),
(2), (4) Date: Sep. 8, 2008

(87) PCT Pub. No.: WO2007/032721
PCT Pub. Date: Mar. 22, 2007

(65) Prior Publication Data
US 2009/0287134 A1    Nov. 19, 2009

Related U.S. Application Data

(60) Provisional application No. 60/716,621, filed on Sep. 13, 2005.

(30) Foreign Application Priority Data

Sep. 13, 2005  (SE) ...................................... 0502030

(51) Int. Cl.
*A61M 37/00*  (2006.01)
*B01D 21/30*  (2006.01)

(52) U.S. Cl. ........................................ 604/5.04; 210/137
(58) Field of Classification Search ........ 604/4.01–6.16; 422/44–48; 210/321.8–321.89, 321.9, 137
See application file for complete search history.

(56) References Cited

U.S. PATENT DOCUMENTS

| 4,201,673 A | 5/1980 | Kanno et al. | |
| 5,238,561 A * | 8/1993 | Sanda et al. | 210/321.8 |

FOREIGN PATENT DOCUMENTS

| DE | 31 44 552 A1 | 5/1983 |
| DE | 31 44 553 A1 | 5/1983 |
| DE | 37 11 695 A1 | 10/1988 |

* cited by examiner

*Primary Examiner* — Leslie Deak
*Assistant Examiner* — Philip Wiest
(74) *Attorney, Agent, or Firm* — Nixon & Vanderhye P.C.

(57) ABSTRACT

Arrangement for extracorporeal circulation of blood having a generally uniform flow diameter where the risk for stagnation of blood is avoided or reduced. The arrangement comprises a generally circular cylindrical means for temporary expanding the flow diameter, a means for flow expansion (9). The means for flow expansion (9) is arranged connecting the bloodline (5) and a component (6, 8) for circulation of the blood. The means for flow expansion (9) comprises a first part with a first flow diameter, d1 and a second part downstream the first part with a second flow diameter d2 where d2/d1≧1.5. The first part has a length extension L1 and the second part has a length extension L2 where L2/L1≧0.5.

36 Claims, 2 Drawing Sheets

ARRANGEMENT FOR EXTRACORPOREAL CIRCULATION OF BLOOD

CROSS REFERENCE TO RELATED APPLICATIONS

This application is a national phase application based on PCT/SE2006/001011, filed Sep. 1, 2006, the content of which is incorporated herein by reference, and claims the priority of Swedish Patent Application No. 0502030-0, filed Sep. 13, 2005, and the benefit of U.S. Provisional Application No. 60/716,621, filed Sep. 13, 2005, the content of both of which is also incorporated herein by reference.

TECHNICAL FIELD

The present invention relates to the field of extracorporeal circulation of blood. More specifically the present invention relates to an arrangement comprising at least one bloodline and at least one component for circulation of blood or blood related fluids, e.g. blood plasma. A dialyzer for use in a dialysis circuit may by way of example constitute the at least one component for circulation of the blood.

BACKGROUND OF THE INVENTION

An arrangement for extracorporeal circulation of blood generally comprises a bloodline and several components for circulation of the blood such as a dialyzer and a drip chamber. In the extracorporeal circuit it is important to avoid stagnation of blood in order to avoid clotting. Clotting may in severe cases lead to dire consequences for the patient.

Extracorporeal circuits of the above kind are for example used in different kinds of medical treatment such as hemodialysis, hemodiafiltration, hemofiltration, plasmapheresis, plasmafiltration, liver dialyis, immunotherapy, irradiation and phototherapy. These extracorporeal circuits have a common feature in that they draw blood from a patient, circulate the blood through a treatment unit and then return the treated blood to the patient. This circulation outside the patients body for treatment begins and ends with the passage of the blood through a single or dual lumen catheter or needle system, generally assisted by a pump to provide a regulated flow of blood throughout the treatment. Such systems most typically use one or more roller pumps to set a specified rate which is carefully monitored and controlled.

In general it is preferable that the entire blood passage through the extracorporeal circuit from a withdrawal needle to the return needle have substantially the same diameter with the possible exception of a dialyzer component so that blood flow velocity is substantially uniform and constant through the circuit. A benefit of an extracorporeal circuit having a uniform inner diameter and substantially continuous flow passages is that the blood tends to flow uniformly through the circuit and does not form stagnant pools within the circuit where clotting may occur.

It has been found that the placement of the bloodline with respect to the inlet to a component for circulation of the blood, e.g. a dialyzer or a drip chamber, influences the distribution of the blood flow in the component. In cases where the bloodline is placed in such a way that the flow of blood is not well distributed so called dead zones may develop where the blood may stagnate and clot. Due to the fact that the bloodline is flexible and loosely dressed on for example a dialysis monitor it is cumbersome to place it in a way that secures a defined distribution of the blood in the component for circulation of the blood.

SUMMARY OF THE INVENTION

An object of the present invention is to provide an arrangement for extracorporeal circulation of blood where a risk for stagnation of blood is avoided or reduced independently of the placement of a bloodline in relation to a component for circulation of blood.

When herein is referred to circulation of blood also other related fluids, e.g. blood plasma, are intended to be covered.

As stated above a conventional arrangement for extracorporeal circulation of blood comprises a channel for circulation of the blood that has a generally uniform inner diameter, a flow diameter. One example embodiment of an arrangement for extracorporeal circulation of blood according to the present invention comprises a temporary expansion of the flow diameter of the channel in which the blood is circulated. The means for expanding the diameter of the flow channel and subsequently restricting it is hereinafter referred to as a means for flow expansion. The means for flow expansion is arranged between the bloodline and the component for circulation of the blood, i.e. upstream the component for circulation of the blood and at its inlet.

The means for flow expansion has a generally circular cylindrical form and a flow channel with a flow diameter. A first part of the means for flow expansion has a first flow diameter, $d1$ and a first length extension $L1$ and a second part has a second flow diameter, $d2$ and a second length extension $L2$, where $d2/d1 \geq 1.5$ and $L2/L1 \geq 0.5$. In a preferred embodiment of the invention the second part of the means for flow expansion has a generally conical form. In one example embodiment the first flow diameter $d1$ corresponds to the inner diameter of the bloodline.

A third length extension $L3$, corresponding to the distance between the means for flow expansion and the component for circulation of the blood, should at a maximum be equivalent to $10 \times d1$.

In one example embodiment of the invention the first flow diameter $d1$ ranges between the following values:

$$0.75 \times d3 \leq d1 \leq d3$$

where $d3$ is the flow diameter of an inlet of the component for circulation of the blood.

The expansion of the flow diameter of the channel in which the blood is circulated secures a mixing of the blood flow to an extent that stagnation is avoided or reduced and the risk of clotting is avoided or reduced.

In one example embodiment of the invention the means for flow expansion is formed as an integrated part of the bloodline.

In one example embodiment of the invention the means for flow expansion is formed as an integrated part of the component for circulation of the blood.

In one example embodiment of the invention the means for flow expansion is comprised in a separate flow device arranged connecting the bloodline and the component for circulation of the blood.

An advantage of the present invention is that a reproducible treatment with decreased variations due to clotting may be provided. Another advantage is that a homogenous blood flow may be assured or improved independently of the placement of the flexible and loosely dressed bloodline in relation to the inlet of the component for circulation of the blood.

Other objects, features, advantages and preferred embodiments of the present invention will become apparent from the following detailed description when taken in conjunction with the enclosed drawings.

DETAILED DESCRIPTION OF THE INVENTION

Figure 1:
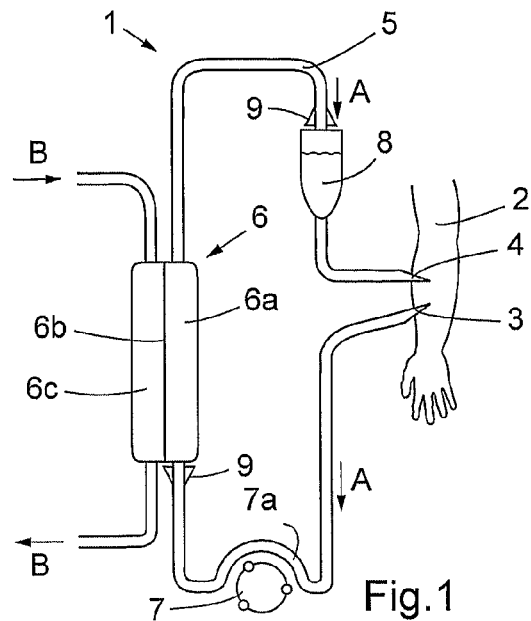
FIG. 1 is a schematic view of an arrangement for extracorporeal circulation of blood.

FIG. 1 shows an arrangement for extracorporeal circulation of blood where a circuit 1 is adapted for circulation of blood outside the body of a patient 2 and designed to be connected to the patient 2 via a single needle or as shown in FIG. 1 via an arterial needle 3 and a venous needle 4. The circuit 1 comprises a line, herein shown as a bloodline 5, and a dialyzer 6. The circuit 1 also comprises a pump 7 for causing the blood to circulate, i.e. flow through the circuit 1. Further the circuit comprises a blood expansion chamber or drip chamber 8 located downstream the dialyzer 6 for securing that no air bubbles are transferred to the patient 2. Upstream and at the inlet of each of the dialyzer 6 and the drip chamber 8 is arranged a means for flow expansion 9.

The treatment of the blood from the patient 2 involves the flow of the blood from the patient into the primary chamber 6a of the dialyzer past a semipermeable membrane 6b located in the dialyzer 6 which separates the primary chamber 6a from a secondary chamber 6c of the dialyzer 6 out of the dialyzer 6 via the drip chamber 8 and back to the patient 2. A replacement fluid is in one example embodiment added to the blood upstream and/or downstream the dialyzer 6 (not shown). Arrows A in FIG. 1 indicate the direction of the blood flow.

A secondary fluid is introduced into the secondary chamber 6c of the dialyzer 6 for controllably collecting material passing across the semipermeable membrane 6b from the blood or for supplying material to pass across the semipermeable membrane 6b into the blood depending on the treatment. Arrows B in FIG. 1 indicate the direction of flow of the secondary fluid through the dialyzer 6.

In an alternative embodiment (not shown) the dialyzer 6 has no inlet for a secondary fluid but only an outlet for fluid filtrated over the membrane.

Figure 2A:
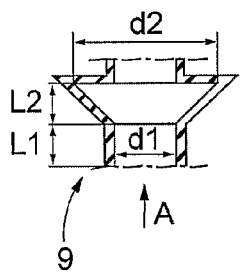
FIGS. 2a-d are example embodiments of a means for flow expansion.

FIG. 2a shows an example embodiment of a means for flow expansion 9 having a generally circular cylindrical form and a flow channel with a flow diameter. The means for flow expansion 9 has a first part and second part where the second part includes in a temporary increased flow diameter. More specifically the first part of the means for flow expansion has a flow diameter d1 and a length extension L1. The second part of the means for flow expansion is arranged downstream the first part and has a maximum flow diameter d2 and a length extension L2. In the disclosed embodiment the second part of the means for flow expansion has a generally conical form.

In the example embodiment of FIG. 2a the ratio of L2/L1 is 1.0 and the ratio of d2/d1 is 2.0. The example embodiment in FIG. 2a includes only one section with an increased flow diameter. The arrow A in FIG. 2a indicates the direction of blood flow.

Figure 2B:
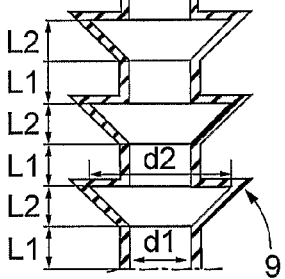

FIG. 2b shows an example embodiment of the means for flow expansion 9 according to FIG. 2a but with two additional means for flow expansion. Thus the means for flow expansion 9 according to FIG. 2b comprises three sections consecutively arranged, where each section shows a first and a second flow diameter d1 and d2 and a first and a second length extension L1 and L2. Each section corresponds to what is described in connection with FIG. 2a.

Figure 2C:
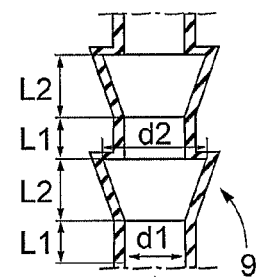

FIG. 2c shows an example embodiment of the means for flow expansion 9 with two consecutive means for flow expansion. Thus the means for flow expansion 9 according to FIG. 2c comprises two sections consecutively arranged where each section shows a first and a second flow diameter d1 and d2 and a first and a second length extension L1 and L2. The ratio of L2/L1 is 1.5 and the ratio of d2/d1 is 1.5.

Figure 2D:
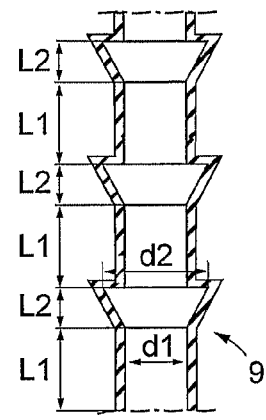

FIG. 2d shows an example embodiment of the means for flow expansion 9 with three consecutive means for flow expansion in the form of three consecutive extended cross section areas. Thus the means for flow expansion 9 according to FIG. 2d comprises three sections consecutively arranged where each section show a first and a second flow diameter d1 and d2 and a first and a second length extension L1 and L2. The ratio of L2/L1 is 0.5 and the ratio of d2/d1 is 1.5.

In one example embodiment of the means for flow expansion 9, d1 ranges between the following values:

$$1.0 \text{ mm} \leq d1 \leq 10.0 \text{ mm}$$

Preferably d1 ranges between the following values:

$$3.0 \text{ mm} \leq d1 \leq 6.0 \text{ mm}$$

In one example embodiment of the means for flow expansion 9, L2 ranges between the following values:

$$0.25(d2-d1) \text{ mm} \leq L2 \leq 3(d2-d1) \text{ mm}$$

Figure 3:
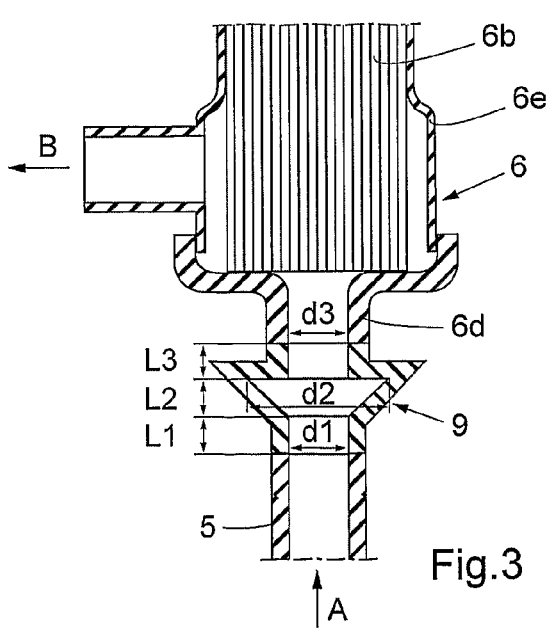
FIG. 3 is an example embodiment of a means for flow expansion according to the principle of FIG. 2a cooperating with an inlet of a dialyzer.

FIG. 3 shows an example embodiment of the means for flow expansion 9 cooperating with a dialyzer inlet sleeve 6d. The means for flow expansion 9 is only schematically shown as a separate flow device arranged connecting the bloodline 5 and the dialyzer 6. The means for flow expansion 9 may alternatively be formed as an integrated part of the bloodline 5 or as an integrated part of the dialyzer 6.

The example dialyzer 6 shown in FIG. 3 comprises a membrane 6b of a hollow fibre type. The pump 7 in FIG. 1 is fluidly connected to the interior of the hollow fibers and adapted to pass blood through them. The dialyzer 6 further includes a housing 6e surrounding the hollow fibers.

Figure 4:
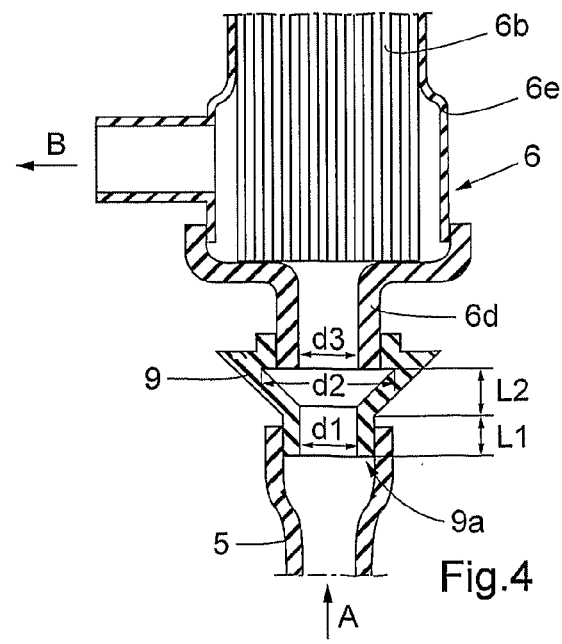
FIG. 4 is an alternative example embodiment of a means for flow expansion according to the principle of FIG. 2a cooperating with an inlet of a dialyzer.

FIG. 4 shows an alternative example embodiment of connection of the means for flow expansion 9 to the dialyzer inlet sleeve 6d. The bloodline 5 is thread over a section of the first part of the means for flow expansion 9 so as to surround it. The flow expansion device 9 is in its turn thread over a section of the dialyzer inlet sleeve 6d so as to surround it. The embodiment shown in FIG. 4 is based on the principle described in connection with FIG. 2a. An edge 9a is provided in the area where blood is entering the means for flow expansion 9 from the bloodline 5. Such an edge 9a is typically too small to generate the advantageous disturbance of the flow pattern. The rest of the features shown in FIG. 4 correspond to those shown in FIG. 3.

The means for flow expansion 9 is arranged at the dialyzer at a distance L3 from the inlet sleeve 6d, where L3 is 0 to 10×d1. In the example embodiment shown in FIG. 4 L3=0.

In one example embodiment of the invention a third flow diameter d3 of an inlet of the inlet sleeve 6d corresponds to the first flow diameter d1 as shown in FIGS. 3 and 4.

Figure 5:
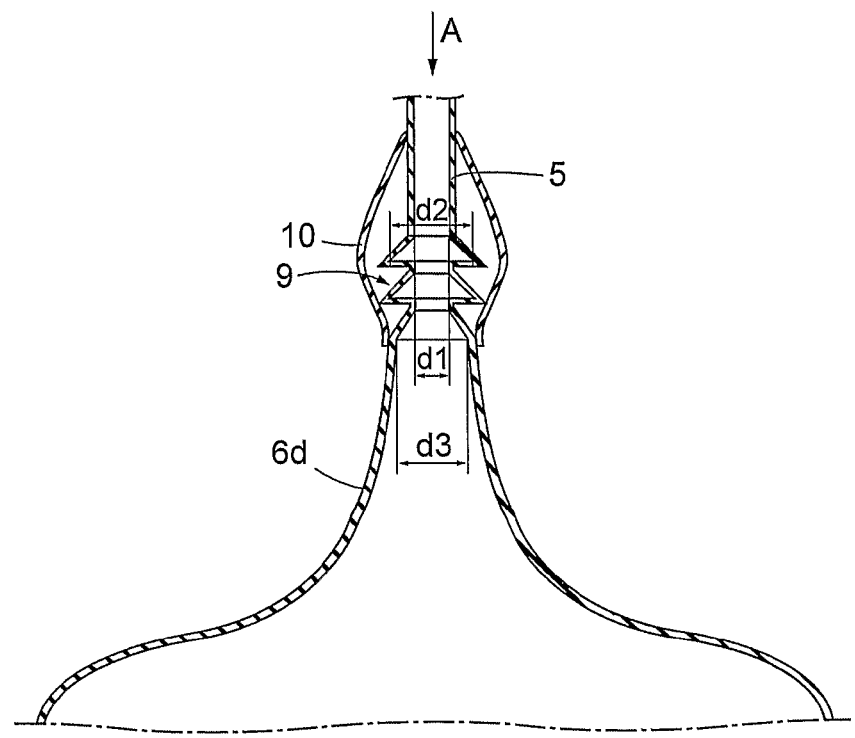
FIG. 5 is a further alternative example embodiment of a means for flow expansion according to the principle of FIG. 2c cooperating with an inlet of a dialyzer.

FIG. 5 shows a further alternative embodiment of the invention where the means for flow expansion 9 has an alternative connection to the inlet sleeve 6d. In the embodiment shown in FIG. 5 the blood enters the inlet sleeve 6d from above as indicated by arrow A. The means for flow expansion 9 is based on the principle described in connection with FIG. 2c. The means for flow expansion 9 is arranged between the inlet sleeve 6d and the bloodline 5. A protective sleeve 10 encloses the means for flow expansion 9. In this example embodiment of the invention the flow diameter d1 is smaller than the flow diameter d3 of the inlet of the inlet sleeve 6d. In one example embodiment the flow diameter d1 corresponds to 0.75×d3.

Figure 6:
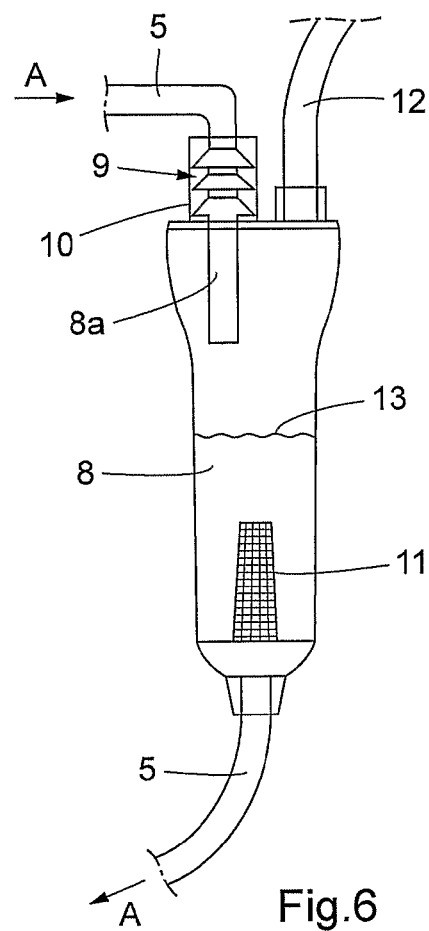
FIG. 6 is an example embodiment of a means for flow expansion according to the principle of FIG. 2b cooperating with an inlet of a drip chamber.

FIG. 6 shows a component for circulation of the blood in the form of a conventional drip chamber 8. The direction of the blood flow is indicated by arrow A. The means for flow expansion 9 is arranged between the bloodline 5 and an inlet sleeve 8a corresponding to the inlet sleeve 6d described in connection with FIG. 3-5. The means for flow expansion 9 corresponds to the principle described in connection with FIG. 2b. The conventional drip chamber 8 comprises a filter in the form of a net 11 through which the blood has to pass before exiting the drip chamber 8 and a gas evacuation line 12 for evacuating any gas separated from the blood circulated via the drip chamber 8. Reference number 13 indicates a blood level in the drip chamber 8.

The means for flow expansion 9 is arranged at the inlet sleeve 6d of the dialyzer 6 and/or at the inlet sleeve 8a of the drip chamber 8.

In operation the arrangement 1 for extracorporeal circulation of the blood according to FIG. 1 circulates the blood through the means for flow expansion 9. In the following the means for flow expansion 9 will be referred to as being arranged at a dialyzer 6 according to e.g. FIG. 3 and/or at a drip chamber 8 according to FIG. 6.

The flow in the blood line 5 is generally uniform and laminar. This implies that there is no cross mixing between single flow layers. The means for flow expansion 9 provides a temporary expanded flow diameter and thereby a disturbance of the flow. The expanded flow diameter d2 is followed by a restricted flow diameter. The restricted flow diameter is generally provided by the flow diameter d3 of the inlet of the inlet sleeve 6d or by the flow diameter d1 of a consecutively arranged flow expansion section of the means for flow expansion 9. The disturbance of the flow implies cross exchange between the flow layers. The flow disturbance upstream the dialyzer 6 and/or the drip chamber 8 improves the flow pattern in the dialyzer 6 and/or the drip chamber 8 such that the flow is well distributed. Due to the cross exchange between flow layers the residence time for each portion of the blood in the inlet sleeve 6d, 8a of the dialyzer 6 and/or the drip chamber 8 is the same with the means for flow expansion 9 than is the case for laminar flow. This means that no portion of the blood resides longer than another portion. Thus the risk for stagnation of blood in the dialyzer 6 and/or in the drip chamber 8 is avoided or reduced independently of the position of the connected bloodline 5.

Typical blood flow rates relevant for the present invention are in the range of 20-4000 ml/min.

The invention is not limited to the described embodiments but may be varied and modified within the scope of the following claims.

The invention claimed is:

1. An arrangement for extracorporeal circulation of a blood related fluid in a circuit, the circuit comprising a bloodline and at least one component for circulation of the blood related fluid having an upstream inlet to the component, wherein the circuit comprises a flow expansion, the flow expansion comprising a first part having a first flow diameter d1 and a first length extension L1 and a second part downstream the first part having a second flow diameter d2 and a second length extension L2 where $d2/d1 \geq 1.5$ and $L2/L1 \geq$ is 0.5 and wherein the second flow diameter d2 is a maximum diameter of a flow passage in the second part and the diameter of the flow passage in the second part gradually expands from d1 to d2 along L2, and further wherein the flow passage in the second part includes a ledge at which the diameter d2 is abruptly changed to a smaller flow diameter, said ledge disposed upstream of the inlet of the component.

2. An arrangement according to claim 1, wherein $L2 \geq 0.25 (d2-d1)$ mm and $L2 \leq 3 (d2-d1)$ mm.

3. An arrangement according to claim 2, wherein $d1 \geq 1$ mm and $d1 \leq 10$ mm.

4. An arrangement according to claim 2, wherein $d1 \geq 3$ mm and $d1 \leq 6$ mm.

5. An arrangement according to claim 1 wherein the $d1 \geq 1$ mm and $d1 \leq 10$ mm.

6. An arrangement according to claim 1 wherein the flow expansion is integral with the bloodline.

7. An arrangement according to claim 6, wherein the flow expansion is integral with the component for circulation of the blood related fluid.

8. An arrangement according to claim 6, wherein the flow expansion is a discrete flow device arranged connecting the bloodline and the component for circulation of the blood related fluid.

9. An arrangement according to claim 6, wherein the flow expansion is arranged at a distance L3 from the inlet of the component for circulation of the blood related fluid, where $L3 \leq 10\, d1$.

10. An arrangement according to claim 1 wherein the flow expansion is integral with the component for circulation of the blood related fluid.

11. An arrangement according to claim 10, wherein the flow expansion is in a flow device arranged connecting the bloodline and the component for circulation of the blood related fluid.

12. An arrangement according to claim 10, wherein the flow expansion is arranged at a distance L3 from the inlet of the component for circulation of the blood related fluid, where $L3 \leq 10\, d1$.

13. An arrangement according to claim 10, wherein the component for circulation of the blood related fluid is selected from a group including: a dialyzer and a drip chamber.

14. An arrangement according to claim 1 wherein the flow expansion is a discrete flow device arranged connecting the bloodline and the component for circulation of the blood related fluid.

15. An arrangement according to claim 14, wherein the flow expansion is arranged at a distance L3 from the inlet of the component for circulation of the blood related fluid, where $L3 \leq 10\, d1$.

16. An arrangement according to claim 1, wherein the flow expansion is at a distance L3 from the inlet of the component for circulation of the blood related fluid where $L3 \leq 10\, d1$.

17. An arrangement according to claim 16, wherein the flow diameter d1 ranges between the following values: $0.75\, d3 \leq d1 \leq d3$, where d3 is the flow diameter of the inlet of the component for circulation of the blood related fluid.

18. An arrangement according to claim 1, wherein the component for circulation of the blood related fluid is selected from a group including: a dialyzer and a drip chamber.

19. An arrangement according to claim 1, wherein the flow diameter d1 ranges between the following values: 0.75 d3≦d1≦d3, where d3 is the flow diameter of the inlet of the component for circulation of the blood related fluid.

20. An arrangement according to claim 1, wherein d1≧3 mm and d1≧6 mm.

21. A flow expansion device for an extracorporeal blood circuit having a bloodline coupled through the flow expansion device to an inlet of a component of the blood circuit, the flow expansion device comprising:
an upstream flow passage having a flow diameter d1 and a length L1;
a downstream flow passage having a length L2, where L2/L1≧0.5, wherein the downstream flow passage gradually increases in diameter from d1 to d2, and d2/d1≧1.5, and
wherein the flow passage in the downstream flow passage includes an abrupt diameter change from d2 to a flow diameter of no greater than d1 no greater than d1, said abrupt change happening upstream of the component inlet.

22. The flow expansion device of claim 21 wherein the upstream flow passage and the downstream flow passage are repeated and followed by a second upstream flow passage and a second downstream flow passage.

23. The flow expansion device according to claim 22 wherein L2≧0.25 (d2−d1) mm and L2≦3 (d2−d1) mm.

24. The flow expansion device according to claim 22 wherein the d1≧1 mm and d1≦10 mm.

25. The flow expansion device according to claim 22 wherein the flow expansion device is integral with the bloodline.

26. The flow expansion device according to claim 22 wherein the flow expansion device is integral with the inlet to the component.

27. The flow expansion device according to claim 22 wherein the flow expansion device is a discrete flow device having an inlet connectable to the bloodline and an outlet connectable to the inlet of the component.

28. The flow expansion device according to claim 22 wherein the flow expansion device is at a distance L3 from the inlet of the component and L3≦10 d1.

29. The flow expansion device according to claim 22 wherein the component is selected from a group including a dialyzer and a drip chamber.

30. The flow expansion device according to claim 22 wherein the flow diameter d1 is within a range device by: 0.75 d3≦d1≦d3, where d3 is the flow diameter of the inlet of the component.

31. The flow expansion device according to claim 22 wherein d1≧3 mm and d1≧6 mm.

32. A method to induce turbulence in blood flow through a blood passage in an extracorporeal blood circuit, wherein the blood passage includes a flow expansion device and a blood treatment component, the method comprising:
withdrawing blood from a patient into the blood passage;
moving the withdrawn blood in a laminar flow through the blood passage and to the flow expansion device;
maintaining the blood in the laminar flow as the blood passes through an upstream flow passage of the flow expansion device having a constant flow diameter d1 and a length L1;
moving the blood through a gradually increasing diameter of the flow expansion device in a downstream flow passage of the flow expansion device, wherein the diameter increases from d1 to d2, wherein d2/d1≧1.5 and the length L2 of the downstream flow passage at least 0.5 the length of L1;
inducing turbulence in the flow of the blood passing through the downstream flow passage of the flow expansion device by passing the blood over an annular ledge formed by abruptly narrowing the flow diameter from d2 to a diameter no greater than d1;
directing the turbulent blood flow to the blood treatment component, wherein the annular ledge is upstream of the inlet of the blood treatment component, and
returning the treated blood from the blood treatment component to the patient.

33. The method to induce turbulence in blood flow in claim 32 wherein the step of inducing turbulence passing the blood over a plurality of the annular ledges wherein each annular ledge has an associated one of the upstream flow passage and the downstream flow passage.

34. The method to induce turbulence in blood flow in claim 32 wherein L2≧0.25 (d2−d1) mm and L2≦3 (d2−d1) mm.

35. The method to induce turbulence in blood flow in claim 32 wherein the flow expansion device is a discrete flow device and the method includes connecting an inlet to the flow expansion device to a bloodline of the blood passage and an outlet of the flow expansion device to the blood treatment component.

36. The method to induce turbulence in blood flow in claim 32 wherein the component is selected from a group including a dialyzer and a drip chamber.

\* \* \* \* \*